(12) United States Patent
Azzazy et al.

(10) Patent No.: US 10,175,175 B2
(45) Date of Patent: Jan. 8, 2019

(54) CHEMOSENSORS, COMPOSITIONS AND USES THEREOF

(71) Applicant: THE AMERICAN UNIVERSITY OF CAIRO, New Cairo (EG)

(72) Inventors: Hassan Azzazy, New Cairo (EG); Ahmed Shahat, New Cairo (EG); Hassan M. A. Hassan, New Cairo (EG)

(73) Assignee: THE AMERICAN UNIVERSITY IN CAIRO, New Cairo (EG)

( * ) Notice: Subject to any disclaimer, the term of this patent is extended or adjusted under 35 U.S.C. 154(b) by 4 days.

(21) Appl. No.: 14/766,187

(22) PCT Filed: Feb. 11, 2014

(86) PCT No.: PCT/IB2014/000930
§ 371 (c)(1),
(2) Date: Aug. 6, 2015

(87) PCT Pub. No.: WO2014/125383
PCT Pub. Date: Aug. 21, 2014

(65) Prior Publication Data
US 2015/0369746 A1 Dec. 24, 2015

Related U.S. Application Data

(60) Provisional application No. 61/763,068, filed on Feb. 11, 2013.

(51) Int. Cl.
*G01N 21/00* (2006.01)
*G01N 21/78* (2006.01)
*G01N 33/18* (2006.01)
*G01N 33/20* (2006.01)
*B01J 31/16* (2006.01)

(52) U.S. Cl.
CPC ......... *G01N 21/78* (2013.01); *G01N 33/1813* (2013.01); *G01N 33/20* (2013.01); *B01D 2253/204* (2013.01); *B01J 31/1691* (2013.01); *Y10T 436/16* (2015.01); *Y10T 436/173845* (2015.01); *Y10T 436/19* (2015.01)

(58) Field of Classification Search
CPC ..................................................... G01N 21/78
USPC .......................................................... 436/73
See application file for complete search history.

(56) References Cited

U.S. PATENT DOCUMENTS 2,877,094 A 3/1959 Khym

FOREIGN PATENT DOCUMENTS

| JP | 2006160155 | 12/2007 |
|----|------------|---------|
| JP | 2006160156 | 12/2007 |
| JP | 2007064182 | 9/2008 |

OTHER PUBLICATIONS

Schaate et al. (Chem. Eur. J. 2011, 17, 9320-9325).*

(Continued)

*Primary Examiner* — Christine T Mui
*Assistant Examiner* — Emily R. Berkeley
(74) *Attorney, Agent, or Firm* — Klauber & Jackson LLC

(57) ABSTRACT

Novel Zr-based metal-organic framework (MOF) chemosensors useful for detection, recognition, removal, and separation of heavy metals are provided. Also provided are methods for preparation of the chemosensors and processes for detection, recognition, removal, and separation of heavy metals using the chemosensors.

9 Claims, 10 Drawing Sheets

(56) References Cited

OTHER PUBLICATIONS

Figure 1:
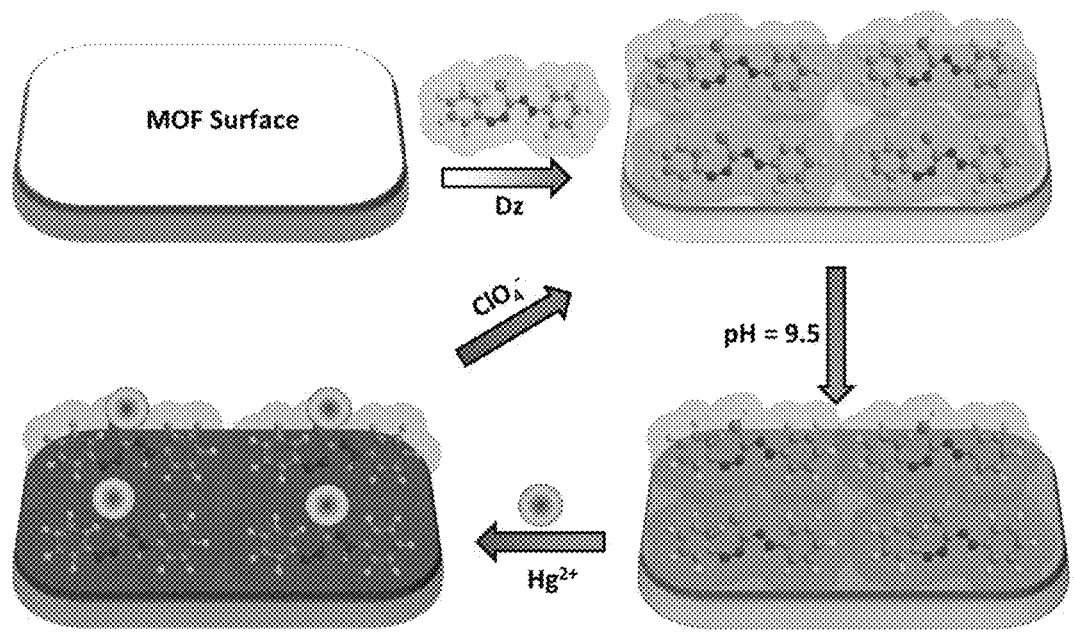

Cheng et al., "Dithizone modified magnetic nanoparticles for fast and selective solid phase extraction of trace elements in environmental and biological samples prior to their determination by ICP-OES", Talanta, 2012, 88:507-15.
Schaate et al., "Porous interpenetrated zirconium-organic frameworks (PIZOFs): a chemically versatile family of metal-organic frameworks", Chemistry, 2011, 17:9320-5.
Giakisikli et al., "Magnetic materials as sorbents for metal/metalloid preconcentration and/or separation. A review", Anal Chim Acta, 2013, 789:1-16.
Shahat et al., "Optical metal-organic framework sensor for selective discrimination of some toxic metal ions in water", Anal Chim Acta, 2013, 793:90-8.

* cited by examiner

CHEMOSENSORS, COMPOSITIONS AND USES THEREOF

CROSS REFERENCE TO RELATED APPLICATIONS

The present application is a National Stage Application which claims priority under 35 U.S.C. § 120 from copending PCT Application No. PCT/IB2014/000930, filed Feb. 11, 2014, which in turn claims priority under from 35 U.S.C. § 119(e) from U.S. Provisional Application Ser. No. 61/763,068, filed Feb. 11, 2013, each of which applications is herein specifically incorporated by reference in its entirety.

FIELD OF THE INVENTION

Provided herein are novel Zr-based metal-organic frameworks (MOF) chemosensors useful for detection, recognition, removal, and separation of heavy metals. Also provided are methods for preparation of the chemosensors and processes for detection, recognition, removal, and separation of heavy metals using the chemosensors.

BACKGROUND OF THE INVENTION

Environmental contamination of Hg(II) and Pb(II) can result in poisoning and death [(a) Sherif A. et al., *Trends in Analytical Chemistry*, 2012, 38, 98. (b) Cheng Z. et al., *Foland, Appl. Geochem*, 2005, 20, 353] or severe damage to the brain [Mason R. P., et al., *Water Air Soil Pollut.*, 1995, 80, 915], kidneys, nervous system, and red blood cells [Toplan S., et al., *J. Trace Elements Med. Biol.*, 2004, 18, 179]. Governments throughout the world are continuing to tighten contaminant concentration limits and guidelines of heavy metals ((HMs) for industrial and environmental waters. Additionally, the World Health Organization recommends the standard allowance for water quality to be less than 10 ppb for Pb, Cd, Hg, and other toxic metal ions. Despite the increasing demands for simple and rapid monitoring of HMs in water, the sensitivities of commercial methods are insufficient to meet the recommended concentration guidelines [Nora Savage et al., (eds.), *Nanotechnology Applications for Clean Water*, 2009, 417-425. William Andrew Inc].

There are urgent needs for simple, inexpensive, sensitive and selective detection of metal ions for a wide range of applications including industrial process management, chemical threat detection, medical diagnostics, food quality control and environmental monitoring. The use of simple, inexpensive, rapid responsive and portable sensors would allow large scale monitoring of heavy metals [(a) Sherif A. et al., *Microporous and Mesoporous Materials* 2013, 166, 195-205 (b) Miyawaki A., et al., *Nature* 1997, 388, 882; (a) Sherif A. et al., *Talanta* 2012, 98, 69-78 (b) Oehme, I., et al., *Mikrochim. Acta,* 1997, 126, 177; (a) El-Safty S. A., et al., *Sensors and Actuators B,* 2013, 176, 1015, (b) Buhlmann P. et al., *Chem. Rev.,* 1998, 98, 1593, (a) Shenashen M. A. et al., *Journal of Hazardous Materials,* 2013, 244-245, 726, (b) Keith, L. H. et al., *Chem. Rev.,* 2007, 107, 2695; (a) El-Safty S. A. et al., *Talanta* 2011, 83, 1341-1351 (b) Sherif A. et al., *Sensors and Actuators B* 2012, 166-167, 253-263 (c) Spichiger-Keller U. S., *Chemical sensors and biosensors for medical and biological applications.* Wiley-VCH, 1998, Weinheim, Germany]. In comparison with other spectroscopic methods, the use of a colorimetric detection method is simple and eliminates the need for sophisticated instruments since results can be detected by "naked-eye".

The determination of HMs in the aquatic environment is of tremendous interest due to their hazardous effects on the ecosystem and ultimately human health. Chemical sensor technologies that specifically detect cations or anions are based on chemical recognition of HMs and subsequent transduction of the analytical signal. Colorimetric sensors are based upon detection of an analyte-induced color change in the sensor materials [Gunnlaugsson T. et al., *Org. Lett.* 2004, 6(10), 1557; Martinez R. et al., *Org. Lett.* 2005, 7(26), 5869; Oehme I. et al., *Microchim. Acta* 1997, 126(3), 177]. Colorimetric sensing systems allow sensitive and simple signal detection while eliminating the need for sophisticated equipment or well-controlled environments. Sensing responses in terms of sensitivity, selectivity, and fast response-time of the chemosensors are induced by the immobilized indicator chromogen "molecular probe"—analyte "cation" interactions [(a) El-Safty S. A., et al., *Sensors and Actuators B,* 2013, 176, 1015, (b) Buhlmann P. et al., *Chem. Rev.,* 1998, 98, 1593]. These binding events transduce signaling responses that have posed considerable constraints based on the chemosensor design. Recently, the ability to manipulate chromophore probes into nanoscale materials as sensing receptors has received attention in the design of flexible chemosensors for recognition of several species such as metal cations [(a) Wirnsberger G. et al., *Chem. Commun.* 2001, 119; (b) Nicole L. et al., *Chem. Commun.* 2004, 2312; (a) Balaji T. et al., *Angew. Chem. Int. Ed.* 2006, 45, 7202; (b) El-Safty S. A. et al., *Chem. Eur. J.* 2007, 13, 9245; (c) El-Safty S. A. et al., *Adv. Func. Mater.* 2007, 17, 3731; (d) El-Safty S. A. et al., *Phys. Chem. C* 2008, 112, 4825; (e) El-Safty S. A. et al., *Chem Mater* 2008, 20, 2644; (f) El-Safty S. A. et al., *Adsorption* 2009, 15, 227] as well as charged and neutral organic molecules [(a) Comes M. et al., *Adv. Mater.* 2004, 16, 1783; (b) Desacalzo A. B. et al., *J. Am. Chem. Soc.* 2005, 127, 184; (c) Balaji T. et al., *Analyst* 2005, 130, 1162; (d) Metivier R. et al., *J. Mater. Chem.* 2005, 15, 2965. (e) El-Safty S. A. et al., *Adv. Funt. Mater.* 2008, 18, 1739; (f) El-Safty S. A. et al., et al., *Adv. Funct. Mater.* 2008, 18, 1485; (g) El-Safty S. A. *J. Mater. Sci.* 2009, 44, 6764].

The immobilization of the indicator chromogen is a crucial step in the preparation of optical chemical sensors for practical applications. The indicator chromogen can be physically immobilized on the support matrixes [Xu H. et al., *Anal. Chem.,* 2001, 73, 4124; Plaschke M. et al., *Anal. Chim. Acta,* 1995, 304, 107; Clark H. A. et al., *Anal. Chem.,* 1999, 71, 4831; Park E. J. et al., *Anal. Chem.,* 2003, 75, 378] or chemically [Shakhsher M. et al., *Anal. Chem.,* 1990, 62, 1758; Lobnik A. *Anal. Chim. Acta,* 1998, 367, 159; Ji J. et al., *Anal. Chem.,* 2004, 76, 1411; Munkholm C. et al., *Talanta,* 1988, 35, 109; Hisamoto H. et al., *Anal. Chem.,* 1998, 70, 1255]. Both of these methodologies have their advantages and disadvantages. Physical entrapment is a simple method, but the sensors prepared will only have a relatively short lifetime because of the leaching of dye molecules into the sample solution [Plaschke M. et al., *Anal. Chico. Acta,* 1995, 304, 107]. Chemical immobilization by covalent binding of indicator chromogen onto the support matrixes is the most efficient technique for obtaining optical chemical sensors with well reproducible response and long lifetime [Hisamoto H. et al., *Anal. Chem.,* 1998, 70, 1255]. The immobilization process involved in the reaction between indicator chromogens and support matrixes, however, suffers from certain shortcomings such as low limit of detection.

Metal organic frameworks (MOFs) have superior tenability and structural diversity as well as chemical and physical properties. MOFs are extended crystalline coordination polymers built from the combination of multitopic organic linkers and metal—oxo clusters as nodes. The modular, organic and inorganic, nature of these porous materials facilitates chemical manipulations aimed at fine tuning of the structures and functions of metal-organic frameworks to make them suitable for specific applications [Wang Z. et al., *Chem. Soc. Rev.* 2009, 38, 1315]. Because of their large internal surface areas, extensive porosity, and high degree of crystallinity, MOFs are comparable to traditional porous materials. Studies on the design, synthesis, and characterization of MOFs have been developing rather quickly to explore their promising various applications in magnetism, luminescence, gas adsorption, sensors, and heterogeneous catalysis [De Sa G. F. et al., *Coord. Chem. Rev.*, 2000, 196, 165; Silvio Q. et al., *Inorg. Chem.*, 2004, 43, 1294; B€unzli J. C. G. et al., *Chem. Rev.*, 2002, 102, 1897; Plecnik C. E. et al., *Acc. Chem. Res.*, 2003, 36, 499; El-Shall M. S. et al., *Mater. Chem.*, 2009, 19, 7625; Sun Y. Q. et al., *Angew. Chem., Int. Ed.,* 2005, 44, 5814].

The crystalline nature and the associated structural regularity of MOFs allow exploration of the relationship between structure and various properties. Additionally, molecules confined in a uniform restricted space exhibit unique properties that are not realized in the bulk state. The uniform pore space of MOFs may, therefore, be exploited to conduct chemical reactions or stabilize reaction intermediates.

Unfortunately, preparation of optimal chemosensors useful for detection and removal of HMs still remains highly challenging.

Thus, there remains a need to make new chemosensors and for novel methods to detect and remove heavy metals. The compositions, and methods described herein are directed toward this end.

SUMMARY OF THE INVENTION

In certain aspects, provided herein are compositions of chemosensors comprising Zr based metal-organic frameworks (Zr-MOF).

In another aspect, provided here are methods of preparation of chemosensors comprising Zr based metal-organic frameworks (Zr-MOF).

In yet another aspect, provided here are methods for detection, recognition, separation, or removal of heavy metals using chemosensors comprising Zr based metal-organic frameworks (Zr-MOF).

In one embodiment, the chemosensor comprises Zr-bdc (UiO-66) MOF.

In one particular embodiment, the chemosensor comprises Zr-bdc (UiO-66) MOF/dithizone (DZ) chromophore.

Other objects and advantages will become apparent to those skilled in the art from a consideration of the ensuing detailed description.

FIGURES

FIG. 1: Art Figure for the detection pathway.

Figure 2:
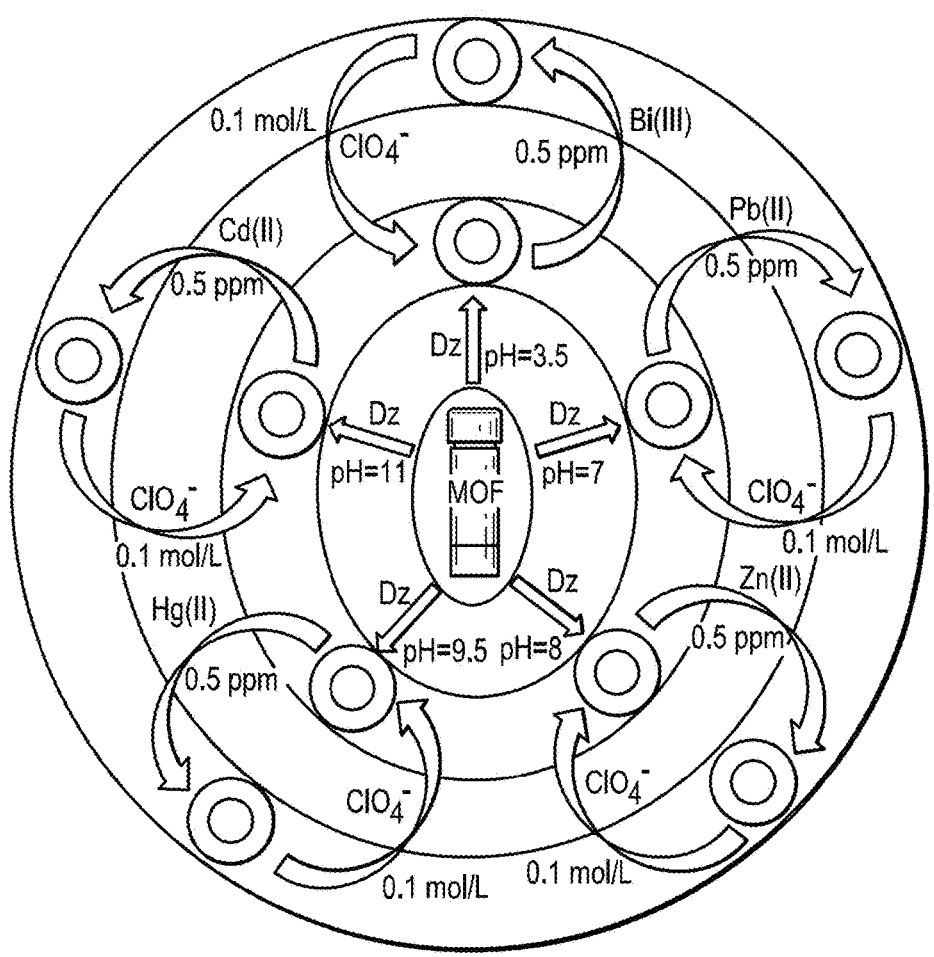

FIG. 2: (Scheme 1) Representative design of the UiO-66 sensor by direct constructing the dithizone (Dz) probe with possible interactions into UiO-66 structure and the optical signaling responses of the UiO-66 sensor for Bi(III), Pb(II), Zn(II), Hg(II) and Cd(II) ions with the formation of the [M(Dz)$_n$]$^{n+}$ chromophore, and the reversible process by using 0.1 M ClO$_4^-$ solution for several times.

Figure 3:
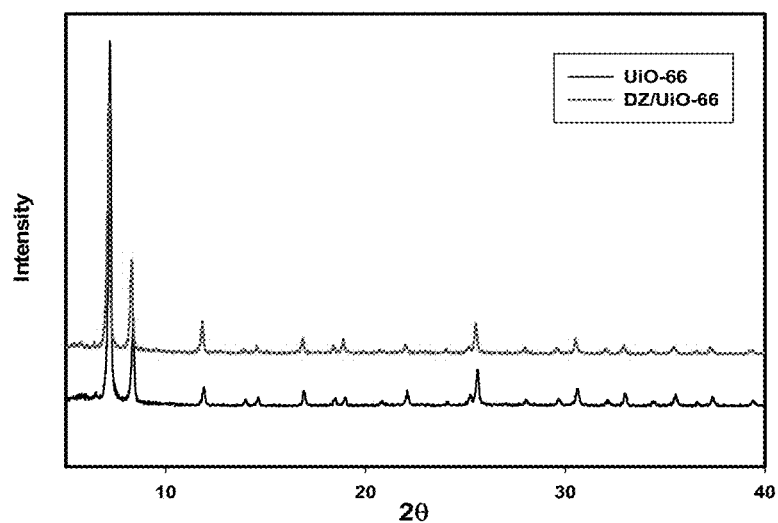

FIG. 3: The X-ray powder diffraction patterns of UiO-66 and the UiO-66 sensor.

Figure 4:
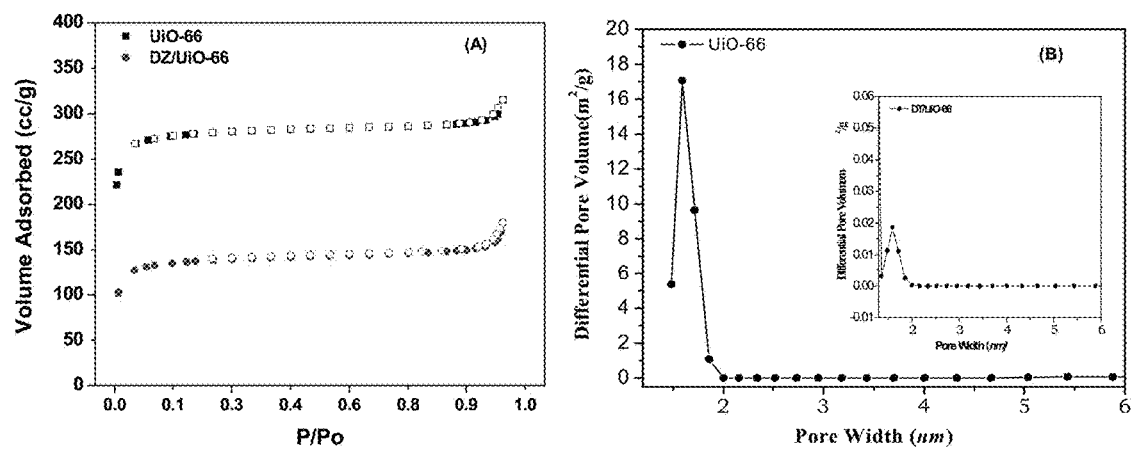

FIG. 4A-B: Nitrogen adsorption isotherms and pore size distribution of (A) UiO-66 and (B) the UiO-66 sensor.

FIG. 5A-B: FESEM images of (A) UiO-66 and (B) the UiO-66 sensor.

Figure 6:
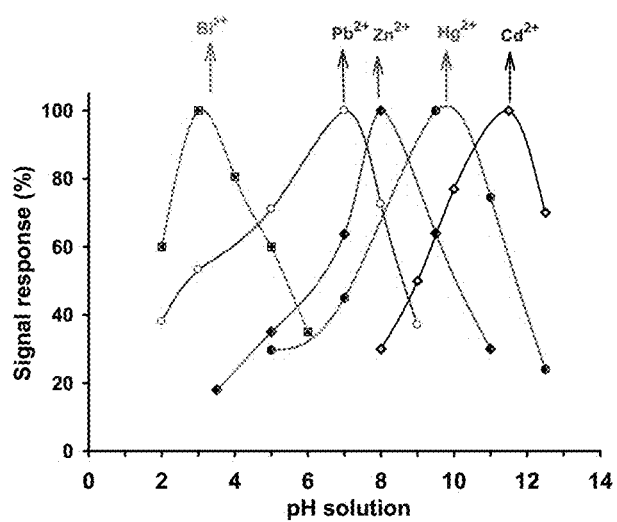

FIG. 6: Signal response of multi-metals detection as a function of pH value using the UiO-66 sensor. Note that the Pb$^{2+}$, Zn$^{2+}$ and Hg$^{2+}$ ions can also be detected using our sensor at pH 5, 6 and 7, after complete masking the active ions toward one ion-sensor, respectively.

FIG. 7A-E: The absorbance spectra observed for the UiO-66 sensor with increasing concentrations of (A) Bi(III), (B) Pb(II), (C) Zn(II), (D) Hg(II) and (E) Cd(II) ions at pH values of 3.5, 7, 8, 9.5 and 11, respectively, and after equilibrating for 1 minute at 25° C. The sensor amount and solution volume were maintained at 5.0 mg and 10 mL, respectively for all sensing systems.

Figure 8:
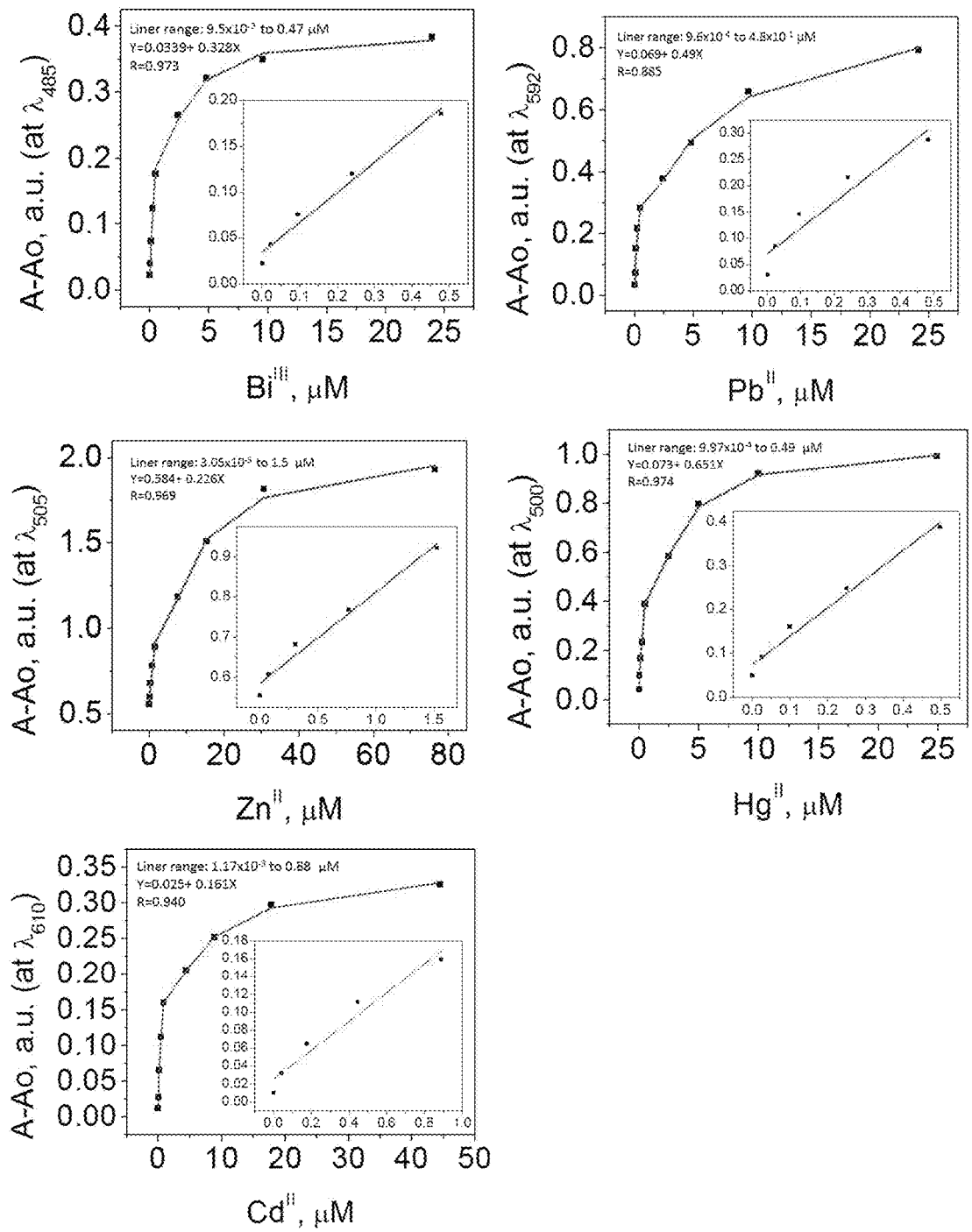

FIG. 8: Calibration plots for the UiO-66 sensor with spectral absorbance measured at $\lambda_{max}$ of 485, 592, 505, 500 and 610 nm with different Bi(III), Pb(II), Zn(II), Hg(II) and Cd(II) ions concentrations.

Figure 9:
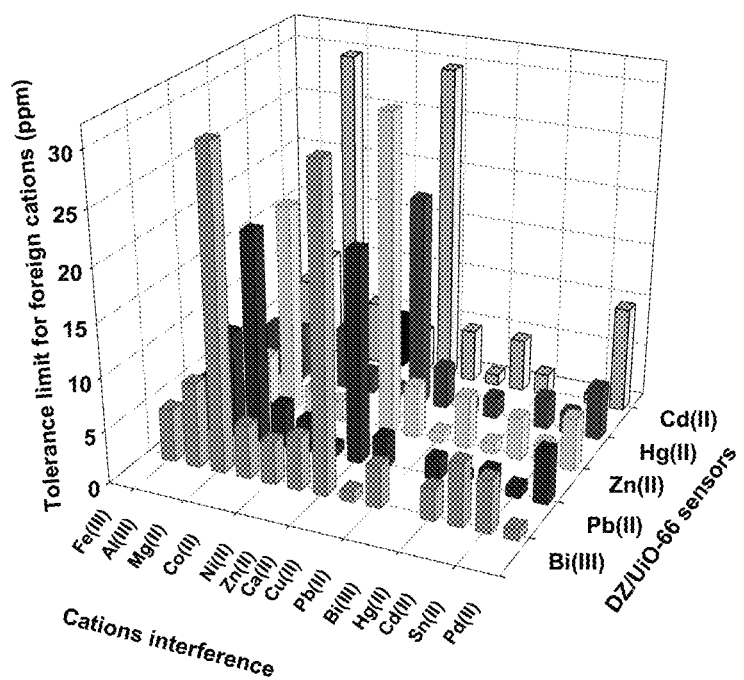

FIG. 9: Tolerance concentrations for interfering matrix species during recognition of [0.5 ppm] of Bi(III), Pb(II), Zn(II), Hg(II) and Cd(II) ions by using their UiO-66 sensor.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Zr-based MOF is Zirconium based metal-organic framework or frameworks.

Zr-BDC MOF or Zr-bdc MOF is Zr-1,4-benzene dicarboxylic acid MOF.

Zr-BPDC MOF or Zr-bpdc MOF is Zr-biphenyl 4,4-dicarboxylic acid MOF.

Zr-TPDC MOF or Zr-tpdc MOF is Zr-terphenyl dicarboxylic acid MOF.

DETAILED DESCRIPTION OF THE PREFERRED EMBODIMENTS

In one aspect, the present invention discloses the use of Zr-based metal-organic frameworks Zr-based MOF chemosensors with micropores geometry, shape and particle morphology as selective carriers for accommodating hydrophobic chromophore probes such as dithizone (DZ) without coupling agent for sensitive and selective discrimination of trace levels of toxic analytes.

In another aspect, the present invention provides chemosensors useful for visual and selective detection of ultra-traces of toxic metal ions. In one embodiment, the chemosensors are Zr-based MOF. In one particular embodiment, the toxic metal ions are Bi(III), Zn(II), Pb(II), Hg(II), or Cd(II). In another embodiment, the chemosensors of the present invention are enabled to design a *facile* chemo-sensory material with inherent sensitivity and selectivity of a wide range of detectable metals analyte. In one embodiment, the chemosensors of the present invention can detect metal analyte up to $10^{-10}$ mol/dm$^3$ in solution. In another embodiment, the analyte uptake response is very rapid. In another embodiment, the analyte uptake response is in order of seconds.

In certain aspects, provided herein are compositions of a chemosensor comprising Zr based metal-organic frameworks (Zr-MOF) useful for detection, recognition, separation, or removal of heavy metals.

In one embodiment, with respect to the composition, the chemosensor comprises Zr-bdc (UiO-66) MOF, Zr-bpdc MOF, or Zr-tpdc MOF. In a particular embodiment, the chemosensor comprises Zr-bdc (UiO-66) MOF.

In one embodiment, with respect to the composition, the chemosensor comprises Zr-MOF loaded by dithizone (DZ).

In one embodiment, with respect to the composition, the chemosensor comprises Zr-bdc (UiO-66) MOF, Zr-bpdc MOF, or Zr-tpdc MOF each loaded by dithizone (DZ).

In one embodiment, with respect to the composition, the chemosensor comprises Zr-bdc (UiO-66) MOF/DZ, Zr-bpdc MOF/DZ, or Zr-tpdc MOF/DZ chromophore.

In one particular embodiment, with respect to the composition, the chemosensor comprises Zr-bdc (UiO-66) MOF/dithizone (DZ) chromophore.

In one embodiment, with respect to the composition, the chemosensor comprises Zr-bdc (UiO-66)/DZ chromophore prepared by mixing Zr-bdc and DZ. In one embodiment the mixing is carried out in a suitable solvent. In one particular embodiment, the solvent is ethanol.

In one embodiment, with respect to the heavy metals, the heavy metals comprise heavy metal ions.

In one particular embodiment, with respect to the heavy metals, the heavy metals are selected from As(III), Bi(III), Zn(II), Pb(II), Hg(II), and Cd(II).

In one embodiment, with respect to the heavy metals, the metal ions are in dissolved ionic forms.

In particular aspects, provided herein are processes for detection, recognition, separation, or removal of heavy metal ions using a chemosensor of the present invention. In one embodiment, the chemosensor comprises Zr based metal-organic frameworks (Zr-MOF).

In another embodiment, with respect to the process, the chemosensor comprises Zr-bdc (UiO-66) MOF, Zr-bpdc MOF, or Zr-tpdc MOF.

In another embodiment, with respect to the process, the chemosensor comprises Zr-MOF loaded by dithizone (DZ).

In another embodiment, with respect to the process, the chemosensor comprises Zr-bdc (UiO-66) MOF, Zr-bpdc MOF, or Zr-tpdc MOF each loaded by dithizone (DZ).

In another embodiment, with respect to the process, the chemosensor comprises Zr-bdc (UiO-66) MOF/DZ, Zr-bpdc MOF/DZ, or Zr-tpdc MOF/DZ chromophore.

In a particular embodiment, with respect to the process, the chemo sensor comprises Zr-bdc (UiO-66) MOF/DZ.

In one embodiment, with respect to the process, the chemosensor comprises Zr-bdc (UiO-66) MOF/DZ chromophore prepared by mixing Zr-bdc and dithizone (DZ). In one embodiment the mixing is carried out in a suitable solvent. In one particular embodiment, the solvent is ethanol In one embodiment, with respect to the process, the heavy metals comprise heavy metal ions.

In one embodiment, with respect to the process, the heavy metals are selected from As(III), Bi(III), Zn(II), Pb(II), Hg(II), and Cd(II).

In one embodiment, with respect to the process, the metal ions are in dissolved ionic forms.

In one embodiment, with respect to the chemosensors or the process, the heavy metal comprise toxic metal ions.

In one embodiment, with respect to the detection, the detection is a visual detection.

In one embodiment, with respect to the detection, recognition, separation or removal, the detection, recognition, separation or removal occurs in aquatic environment.

In one embodiment, with respect to the detection, the detection is a ultra low level detection.

In another specific aspect, provided herein are methods for preparation of Zr-based chemosensors of the present invention.

In one particular aspect, a facile and effective approach, for the visual detection and removal of ultra-traces of some toxic metal ions such as Bi(III), Zn(II), Pb(II), Hg(II) and Cd(II) is provided. In a particular embodiment, the approach is based on the use of Zr-based metal-organic frameworks (MOF). In a particular embodiment, the MOF is Zr-BDC (UiO-66) sensor. In one embodiment, the approach is based on the micropores geometry, shape and particle morphology of UiO-66. In another embodiment, the approach uses MOF, such as Zr-BDC (UiO-66) sensor as a selective carrier for accommodating hydrophobic chromophore probes such as dithizone (DZ) without any coupling agent. In one embodiment, the chemosensors of the invention can be used as sensitive and selective discrimination of trace level of toxic analytes. In one embodiment, the chemosensors of the invention can be utilized for the detection of ultra-traces of some toxic metal ions with the naked eye. In another embodiment, the novel chemosensors of the invention displays high sensitivity and selectivity of a wide range of detectable metals analytes up to $10^{-10}$ mol/dm$^3$ in solution, in a rapid analyte uptake response (seconds). The chemosensor of the invention developed by the inventors is a stable, cost effective, easy to prepare, and could be useful for rapid detection of ultra-traces of some toxic metal ions such as Bi(III), Zn(II), Pb(II), Hg(II) and Cd(II) ions in water samples. Unlike the previously known sensors, the chemosensor of the invention developed by the inventors can be used to detect plurality of metals. The chemosensors of the invention used for multi-metal detection. The Zr-BDC/DZ chemosensors can visually detect multi metal ions at different pH values in aquatic solution.

In one embodiment, the composition of the present invention can be used as highly sensitive solid sensors for simple and simultaneous naked-eye detection.

In another embodiment, the composition of the present invention can be used for removal of extremely toxic heavy metal ions in aquatic samples. In one embodiment, the the heavy metals are selected from As(III), Bi(III), Zn(II), Pb(II), Hg(II), and Cd(II).

In one embodiment, the composition of the present invention can be used in detection, recognition, separation, or removal of heavy metals.

In one embodiment, the heavy metal is As(III). In another embodiment, the heavy metal is Bi(III). In another embodiment, the heavy metal is Zn(II). In another embodiment, the heavy metal is Pb(II). In another embodiment, the heavy metal is Hg(II). In another embodiment, the heavy metal is Cd(II).

In one embodiment, the composition of the present invention can be used as a chemical sensor for anions like $F^-$, $Cl^-$ and $Br^-$.

In one embodiment, the composition of the present invention can be used as a chemical sensor for ions like $NH_4^+$, $PO4^{-3}$ and $SiO4^{-2}$.

In one embodiment, the composition of the present invention can be used in luminescence, dyes adsorption, sensors, and heterogeneous catalysis.

The Art FIG. 1 describes the pathway of the detection.

Additional embodiments within the scope provided herein are set forth in non-limiting fashion elsewhere herein and in the examples. It should be understood that these examples are for illustrative purposes only and are not to be construed as limiting in any manner.

GENERAL SYNTHETIC PROCEDURES

The compositions provided herein can be prepared from readily available starting materials using the following general methods and procedures. See, e.g., Synthetic Schemes below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compositions provided herein may be isolated and purified by known standard procedures. Such procedures include (but are not limited to) recrystallization, column chromatography or HPLC. All chemicals were used without any further purification. Deionized water was used for all experiments.

Example 1

Preparation of Zr-Based MOF

The Zr-based MOFs can be synthesized following the procedures described by Lillerud, et al. [*J. Am. Chem. Soc.* 2008, 130, 13850] or described in WO2009/133366.
A. Synthesis of Zr-bdc (UiO-66) MOF Zr-bdc (UiO-66) MOF was synthesized by reacting $ZrCl_4$ and 1,4-benzene dicarboxylic acid and following the method described by Lillerud et al.
B. Synthesis of Zr-bpdc (UiO-66) MOF Zr-bpdc (UiO-66) MOF is synthesized by reacting $ZrCl_4$ and biphenyl 4,4-dicarboxylic acid and following the method described in WO2009/133366.
C. Synthesis of Zr-tpdc (UiO-66) MOF Zr-tpdc (UiO-66) MOF is synthesized by reacting $ZrCl_4$ and terphenyl dicarboxylic acid and following the method described in WO2009/133366.

Example 2

Fabrication Design of MOF Sensors of the Invention

Chemosensors of the invention can be fabricated by using direct immobilization of the ethanol solution of 30 mg dithizone (DZ)-probe into 1.0 g Zr-based MOF carrier.

For example, UiO-66/DZ Chemosensor was fabricated by using direct immobilization of the ethanol solution of 30 mg dithizone (DZ)-probe into 1.0 g UiO-66 carrier. Ethanol was removed by evaporation at ambient temperature, leading to the direct attachment of the dye probe into the MOF. The resulting MOF sensors were thoroughly washed with deionized water until no elution of DZ color was observed. The chemosensors were dried at 65° C. for 2 hours. The adsorption capacity (Q, mmol. $g^{-1}$) of the DZ probe at saturation was determined by the following equation; $Q_t=(C_o-C_t) V/m$, where $Q_t$ is the adsorbed amount at saturation time t, V is the solution volume (L), m is the mass of MOF carriers (g), $C_o$ and $C_t$ are the initial concentration and the concentration at saturation time, respectively (see Table 1).

Example 3

Recognition of Ultra-Traces Level of the Metal Ions

The colorimetric determination and visual detection of Bi(III), Pb(II), Zn(II), Hg(II) and Cd(II) ions by using single MOF sensor were carried out over a wide range of pH solutions. A mixture containing specific concentrations of each analyte ions adjusted at pH 2-12 range was added to ~5 mg of the sensor at constant volume (10 $cm^3$). After equilibration, response time ($R_t$, see Table 1), in which the prominent color change and signal saturation in the nanosensor absorbance spectra were achieved, the solid chemosensors were collected by using suction and 25-mm-diameter filter paper. The color of the collected sample was determined by naked-eye and UV-Vis spectrometry.

Example 4

Spectroscopic Information

The absorption spectra of the supermicroporous chemosensors were collected using a Perkin Elmer Lambda 950 model solid-state UV-Vis spectrophotometer. Powder X-ray diffraction (XRD) patterns were measured by using Bruker D8 Discover diffractometer with monochromated CuKα (λ=1.54178 Å) at 40 kV, and 45 mA. The adsorption/desorption isotherms were collected using Quantachrom Autosorb system at 77 K. Prior to analysis, the samples were outgassed at 80° C. for 24 h. The BET surface areas pore volume and pore size distribution were calculated from $N_2$ adsorption data. Field emission scanning electron microscopy (FESEM) was obtained on Zeiss Leo Supra55 microscope. The samples for FESEM observations were observed without any metal coating. The concentrations of metal ions were analyzed by using a Seiko SPS-1500 inductively coupled plasma atomic emission spectrometer (ICP-AES) before and after detection Example 5

Characterization of a Representative Zr-Based Metal-Organic Frameworks (UiO-66) Nanosensor The most common method used for design of optical chemical sensor arrays is the grafting technique [Comes M.

et al., *Adv. Mater.* 2004, 16, 1783]. In this study, the MOF sensor was fabricated via direct inclusion of ethanol solution of dithizone-probe into UiO-66 without use of surface modifiers such as silane- or thiol-coupling agents. However, the removal of ethanol by evaporation at ambient temperature led to create sufficiently physisorbed "short-range" interactions (i.e. van der Waals and H-bonding interactions) between the pore surface of the UiO-66 and the heteroatoms of dithizone molecules (FIG. 2, Scheme 1). Compared with the preliminary design of chemosensors using surface modifications [(a) Comes M. et al., *Adv. Mater.* 2004, 16, 1783; (b) Desacalzo A. B. et al., *J. Am. Chem. Soc.* 2005, 127, 184; (c) Balaji T. et al., *Analyst* 2005, 130, 1162], in which expensive reagents such as thiol- or silane coupling agents were used to tune the polarity of the porous silica surfaces prior to the immobilization of chromophores, this novel optical chemosensor design was successfully fabricated without such coupling agents. Moreover, the direct inclusion of the probe may achieve higher flexibility on the specific activity of the electron acceptor/donor strength of the molecular probe than that obtained by the immobilization method using surface modifiers. Although, the surface modification method enhanced the stability of the sensor due to strong electrostatic interactions 'Coulombic-types' between the probe molecule and charged surfaces, limitations in the electron mobility of the functional site of the receptors may occur [(a) Comes M. et al., *Adv. Mater.* 2004, 16, 1783; (b) Desacalzo A. B. et al., *J. Am. Chem. Soc.* 2005, 127, 184; (c) Balaji T. et al., *Analyst* 2005, 130, 1162]. The direct inclusion approach led to high accessibility of the binding site of the probes. This has led to the generation and transduction of a color signal and a fast response. Furthermore, the organic nature of the MOFs enhances the stability of the sensor due to strong electrostatic interactions 'Coulombic-types' between the probe molecules. This approach, indeed, led to high ligand-binding affinity "electron acceptor/donor strength" with Bi(III), Pb(II), Zn(II), Hg(II) and Cd(II) ions in very fast response (seconds), during the recognition process under the specific pH sensing conditions.

The X-ray powder diffraction (XRPD) patterns obtained for UiO-66 and DZ/UiO-66 materials are depicted in FIG. 3. All the materials show well-defined XRPD patterns corresponding to typical UiO-66 structure [Schaate A. et al., *Chem. Eur.* 1 2011, 17, 6643]. Despite the loading of the organic-probe moieties onto the micropores surface, a typical Bragg diffraction peaks were retained indicating the stability of UiO-66 network under the employment condition. Furthermore, the diffraction intensity both materials were significantly unchanged (FIG. 3).

To evaluate the impact of dithizone-probe (DZ) loading on the porosity of UiO-66, a sample of DZ/UiO-66 were activated by degassing at 80° C. and $10^{-5}$ Torr for 12 hours prior to $N_2$ sorption-desorption measurements. The $N_2$ isotherms depicted in FIG. 4a, ($N_2$ uptake) indicate that there is a significant drop in the surface area of UiO-66. The apparent Brunauer-Emmett-Teller (BET) surface area values were found to be 420.9.7 $m^2/g$ which is almost half that of the parent UiO-66 (838.7 $m^2/g$). The impact of DZ loading on the pore volume was estimated by using the single-point adsorption method at $P/P_o=0.95$. Pore volumes followed a similar trend as surface area (0.245 cc/g) which are significantly lower than the pore volume of the unloaded UiO-66 (0.459 cc/g). The reduction in the pore volume and surface area after loading could be due to the fact that the DZ is deposited inside the microchannels and is well dispersed on the surface of the UiO-66. Additionally, these observations reveal that DZ/UiO-66 sample retain their microporosity, which is a very important aspect that allows for DZ accessibility by substrates. The pore size distribution of pure and DZ loaded UiO-66 shows a unique peak centered at about 1.6 nm diameters (FIG. 4a).

Figure 5:
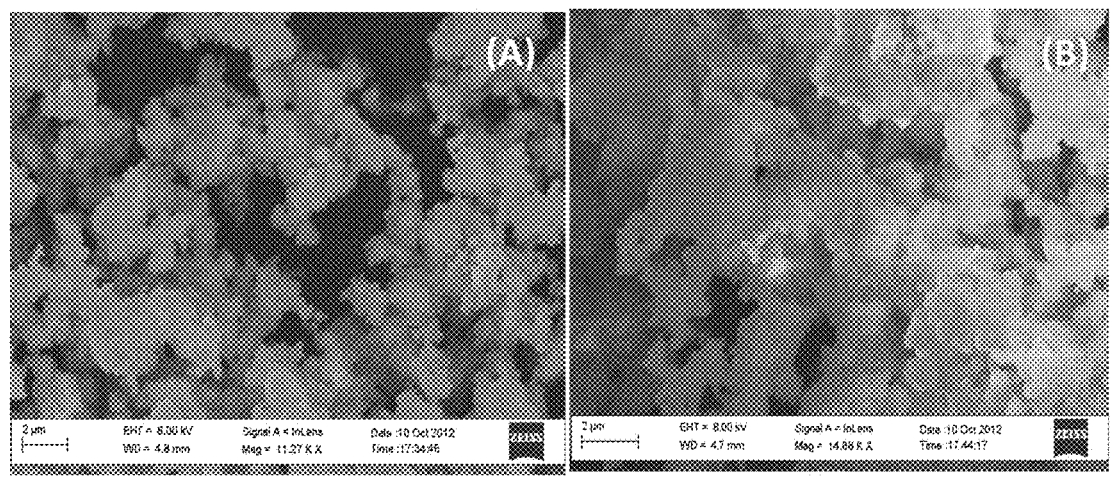

FESEM of the bare UiO-66 and the UiO-66 sensor samples are shown in FIG. 5. Based on the FESEM observations, both materials occur as small cubic inter-growing crystals. In general, results indicated the retention of the structure after loading of the organic-probe moieties into the surface which is consistent with XRPD patterns (FIG. 3)

Example 6

Recognition Process of Multi Metals Using Single, UiO-66 Sensor

The high performance of the sensors depended on key factors such as the contact-time (signal response time), amount of support-based sensor, reaction temperature, and pH [El-Safty, S. A. et al., *Adv. Mater.* 2003, 15(22), 1893-1899; Han M. S. et al., *Angew Chem Int Ed* 2002, 41, 3809; Miyaji H. et al., *Angew Chem Int Ed* 2000, 39, 1777; Rex M. et al., *Anal Chem* 2006, 78, 445; El-Safty S. A. et al., *Chem Eur J* 2007, 13, 9245]. These key factors strongly affect the homogeneity in the color map distribution and intensity even at low loading level of metal ions during visual detection. In general, changes in these key factors can play significant roles involving the redistribution of the charge polarity and the electron and energy transfer within the dithizone probe molecule into the pore surfaces. The chemical sensing system is extremely sensitive to such changes, which in turn, dramatically affect the accuracy and precision in the determination and visual detection of the target ions [Liu J. et al., *J Am Chem Soc* 2004, 126, 12298]. The efficiency of metal ion-sensing with optical sensor was significantly influenced by the pH of the solution (FIG. 6). The absorbance spectra of the [M-probe]$^{n+}$ chromophorees were carefully monitored over a wide range of pH solutions (Table 1). The optical sensor was significantly sensitive in terms of its optical "color intensity" and signal response for Bi(III), Pb(II), Zn(II), Hg(II) and Cd(II) ions at pH 3.5, 7, 8, 9.5 and 11.5, respectively.

The Table 1, below, describes the efficiency of pH sensor in terms of accessibility, sensitivity, response time, and reversibility features during recognition of toxic Bi(III), Pb(II), Zn(IV), Hg(II) and Cd(II) metal ions formed by using dithizone-loaded UiO-66 as carriers at different pH values.

TABLE 1

The efficiency of pH sensor during recognition of toxic metal ions using the representative compositions of the invention

| Metal ions | $D_L$ mol dm$^{-3}$ | $D_R$ mol dm$^{-3}$ | $R_t$ (s) | Probe Wavelength & color | [M-chelation] Wavelength & color | pH range | Specific pH | Sensor Featured with Reuse Cycles | | | | |
|---|---|---|---|---|---|---|---|---|---|---|---|---|
| | | | | | | | | S | Eluent | No. | $t_R$ min | E % |
| Bi$^{3+}$ | 6.06 × 10$^{-9}$ | 9.5 × 10$^{-10}$ To 4.7 × 10$^{-7}$ | 15 | 449 Olive green | 485 Brown | 3-4 | 3.5 | 1:3 | [0.1 mM] ClO$_4^-$ | 2 4 6 | 2 3 5 | 99 98 96 |
| Pb$^{2+}$ | 13.0 × 10$^{-8}$ | 9.6 × 10$^{-10}$ To 4.8 × 10$^{-7}$ | 20 | 588 Green | 592 Orange | 6.5-7.5 | 7 | 1:2 | [0.1 mM] ClO$_4^-$ | 2 4 6 | 3 3 6 | 99 97 95 |
| Zn$^{2+}$ | 20.6 × 10$^{-8}$ | 3.05 × 10$^{-9}$ To 1.53 × 10$^{-6}$ | 20 | 430 Dark yellow | 505 Purple | 7.5-8.5 | 8 | 1:2 | [0.1 mM] ClO$_4^-$ | 2 4 6 | 2 3 4 | 99 97 94 |
| Hg$^{2+}$ | 6.11 × 10$^{-8}$ | 9.97 × 10$^{-10}$ To 4.98 × 10$^{-7}$ | 10 | 420-598 Greenish brown | 500 red | 9-10 | 9.5 | 1:2 | [0.1 mM] ClO$_4^-$ | 2 4 6 | 4 6 7 | 99 96 95 |
| Cd$^{2+}$ | 16.9 × 10$^{-8}$ | 1.77 × 10$^{-9}$ To 8.89 × 10$^{-7}$ | 30 | 457 Brown | 610 Orange | 10.5-11.5 | 11 | 1:2 | [0.1 mM] ClO$_4^-$ | 2 4 6 | 2 3 5 | 99 97 94 |

Limit of detection ($D_L$), detection range ($D_R$), and response-time ($R_t$). The sensing efficiency (E) of the MOF sensors within the recycle numbers was estimated in terms of the sensitivity during the detection of metal ions and ($t_R$) recovery time.

Example 7

Visual Detection of the Metal Ions by UiO-66 Sensor

Despite the feasible use of this commercial receptor dithzone probe for sensitive determination of Bi(III), Pb(II), Zn(II), Hg(II) and Cd(II) ions up to 10$^{-7}$ mol/dm$^3$ [Sandell E. B. *Colormetric determination of traces of metals*. 2nd ed. Interscience Publishers, Inc., New York, 1950], the developed UiO-66 sensor showed remarkable enhancement in the sensitivity and selectivity of these metal ions compared with dithizone molecular dye in solution system. The current sensor design based on UiO-66 shows advanced features. This is because in addition to conventional recognition of these metal ions at trace levels (~10$^{-10}$ mol/dm$^3$) there is a further control of the sensing assay, governed by *facile* handling of signal read-out optical measurements. In addition, the UiO-66 sensor could be used as simple preconcentrators to yield high adsorption capacity and preconcentration efficiency, leading to simultaneously visual inspection and complete removal of these metal ions over a wide, adjustable range concentration. Moreover, still the physical properties of the MOF sensor such as high surface area, porosity, organic nature of the MOFs and the particle-size morphology are advantageous to allow high recognition and binding of the target in sensing assay. Results indicated that the chemical MOF sensor offer one-step and simple sensing procedures for both quantification and visual detection of Bi(III), Pb(II), Zn(II), Hg(II) and Cd(II) ions without the need for sophisticated instruments.

Figure 7:
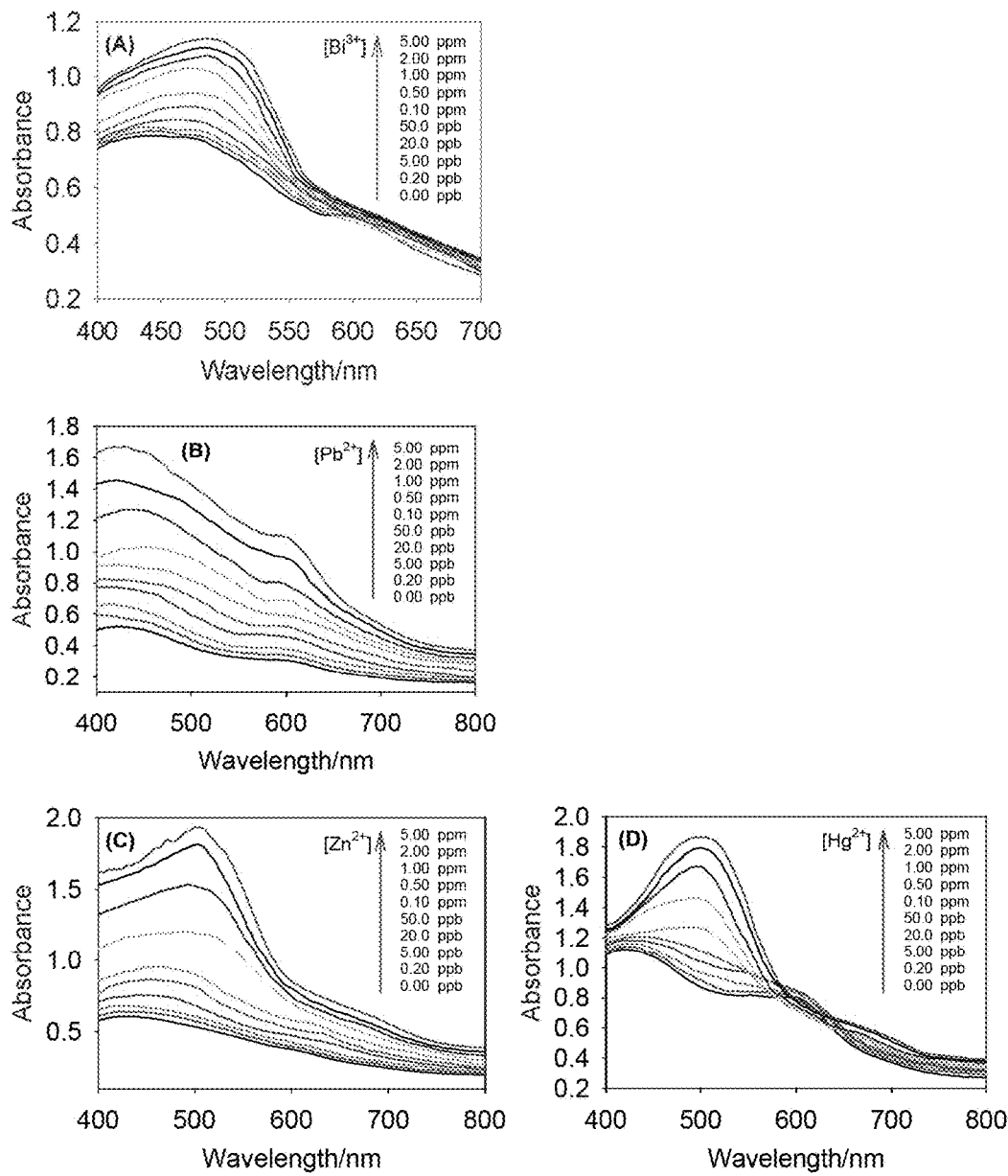
Figure 7:
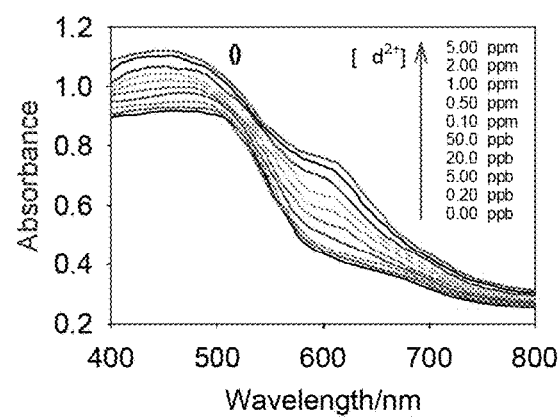

Colorimetric studies using UV-Vis spectroscopy enabled quantitative determination of the specific detection range ($D_R$) of each metal ion-sensing system by monitoring the signaling change in the absorbance spectra of the dithizone sensor with the addition of the analyte ions (for example, FIG. 7). Changes in these spectra are indicators of the metal-receptor binding events to form [metal-receptor] chromophorees (Scheme 1). The charge-transfer reflection band of the chromophore was based on the ligand-binding affinity with central metal ions during the recognition and the nature of the chromophore formation under the specific sensing conditions. The color intensity of the [metal-dithizone]$^{n+}$ chromophorees at the specific wavelengths increased in a liner correlation to the analyte concentrations up to the maximum plateau (saturation step), as evidenced from the calibration curves of the UiO-66 sensing systems.

Example 8

Calibration Graphs and Analytical Parameters

The calibration plots of the UiO-66 sensor, in general, show a linear correlation at low concentration ranges of multi-metal ions (FIG. 8). The linear curves indicated that the metal ions can be detected with highest sensitivity over a wide-range of concentrations. The limit of detection ($L_D$) (Table 1) indicated that the developed optical sensor enabled a better recognition of target ions than that obtained by sensors fabricated by the conventional method. The $L_D$ value indicated that single UiO-66 sensor enabled, for the first time, detection of metal targets up to ~10$^{10}$ mol/dm$^3$, indicating the efficient detection of multiple toxic metal ions (Table 1). In fact, the standard deviation for the analysis of Bi(III), Pb(II), Zn(II), Hg(II) and Cd(II) ions using MOF sensor was of ~0.6%, as evidenced for the fitting plot of the calibration graphs (FIG. 8, inserts). The detection ($L_D$) and quantification ($L_Q$) limits of these metal ions using the MOF sensor were estimated to be 0.88 ppb and 2.9 ppb, respectively, according to the following equation (2) [Christian, G. D. *Analytical Chemistry*, 6th edn. Wiley, New York, 2003].

$$(L_D) \text{ or } (L_Q) = kS_b/m \tag{2}$$

where, $S_b$ and m are the standard deviation and the slope of the linear calibration graph (FIG. 8, inserts), the constant k is equal to 3 and 10 in the case of the determination of $L_D$ and $L_Q$, respectively.

Example 9

Ion-Reversible Sensing Systems

Simple treatment using the stripping agent of ClO$_4^-$ anion at 0.1 mol/L concentration was found to effectively remove the metal ions (i.e. dechromophoreation) (see Scheme 1).

This $ClO_4^-$ eluant has high binding affinity to form stable metal-chromophore more than that of metal-dithizone probe chromophorees. We have carried out these experiments several times via liquid-exchange process to release the metal ions and to get "metal-free" probe surface. After multiple regeneration/reuse cycles (i.e. ≥6) of the [metal-dithizone]$^{n+}$ chromophore, although the metal ion-sensing systems showed a slight influence on the sensitivity with increased recovery time ($t_R$) of metal-to-dithizone ligand binding (Table 1), they showed well-controlled signaling in the quantification and detection of metal ions. Results showed the optical sensor can work even after extended sensing and regeneration cycles ≥30 times.

Example 10

Ion-Selective Sensing Systems

In such pH sensor dependent, the selectivity of the ion-sensing system is crucial. The pH-dependent optical sensor (Table 1 & FIG. 6) shows effective disturbance species at range of concentrations of the active cations on the specific pH range. Results showed that significant changes in visible color patterns and absorbance spectra of sensor were observed, particularly with Pb(II), Zn(II) and Hg(II) ion-sensor. At the pH 7-9.5 range, these three metals show significant interference among each other's. So, we used 0.15 mM of tartrate, thiosulphate and citrate, respectively, as masking agents at specific pH of each ion-sensing system (Table 2 & FIG. 9).

The Table 2, below, describes the Tolerance concentration for interfering matrix species during recognition of [0.5 ppm] Bi(III), Pb(II), Zn(II), Hg(II) and Cd(II) ions by using optical sensor, respectively. Note: The selectivity obtained by sensor within the addition of the competitive interfering foreign ions, electrolyte species and chromophoreing agents prior to each analyte ions under the normal sensing conditions, such as $R_t$, pH 3.5, 7, 8, 9.5 and 11 and at temperature of 25° C.

were evident after storage for relatively long times (i.e. ≥2 months) in a dark bottle. The relatively high storage stability, in principle, indicated the effect of the use of MOFs nano-structures with their open pores and with dithizone probe assembly inside the pores in terms of actively long-term shelf-time of the sensors. Compared with chemosensor design using surface modification, in which strong electrostatic interactions (Coulombic-types) between the probe molecule and charged silica surfaces [(a) Balaji T. et al., Angew. Chem. Int. Ed. 2006, 45, 7202; (b) El-Safty S. A. et al., Chem. Eur. 1 2007, 13, 9245; (c) El-Safty S. A. et al., Adv. Func. Mater. 2007, 17, 3731] occurred, the stability under storage "shelf time" of this solid sensor design is much higher than that sensor design based on physisorbing probe molecules. In general, this novel sensor design using direct inclusion of dithizone probes provided a facile sensing design in terms of sensitivity, selectivity, reproducibility and acceptable degree of stability and shelf time.

The inventors have constructed a highly sensitive novel MOF sensor for simple and simultaneous colorimetric detection and possibly removal of toxic heavy metal ions such as Bi(III), Pb(II), Zn(II), Hg(II) and Cd(II) ions in aquatic samples. The novel UiO-66 sensors comprise dithizone loaded Zr-bdc MOF, Zr-bpdc MOF, and Zr-tpdc MOF. Moreover, the successful design of UiO-66 sensor shows advanced features of a further control of the sensing assay that can be governed by *facile* handling of signal read-out optical measurements at trace levels (~$10^{-10}$ mol/dm$^3$) of these metal ions. The inventors have shown that the UiO-66 sensors of the invention could be used as simple preconcentrators to yield high adsorption capacity and preconcentration efficiency, leading to simultaneous visual inspection and complete removal of these metal ions over a wide, adjustable range concentration. In addition, the UiO-66 sensors provide extraordinary sensitivity, selectivity, reusability, and fast kinetic detection and quantification of Bi(III), Pb(II), Zn(II), Hg(II) and Cd(II) ions. Furthermore, the UiO-66 sensors can provide fast kinetic detection and quantification of As(III) ions.

TABLE 2

Tolerance Limits for Foreign Cations
Tolerance limit for foreign cations (ppm)

| Analytes | Fe$^{3+}$ | Al$^{3+}$ | Mg$^{2+}$ | Co$^{2+}$ | Ni$^{2+}$ | Zn$^{2+}$ | Ca$^{2+}$ | Cu$^{2+}$ | Pb$^{2+}$ | Bi$^{3+}$ | Hg$^{2+}$ | Cd$^{2+}$ | Sn$^{2+}$ | Pd$^{2+}$ |
|---|---|---|---|---|---|---|---|---|---|---|---|---|---|---|
| Bi$^{3+}$ | 5 | 8 | 30 | 5 | 4 | 5 | 30 | 1$^x$ | 4 | Ref. | 3$^x$ | 6 | 5 | 1$^+$ |
| Pb$^{2+}$ | 5 | 10 | 20 | 4 | 3 | 1$^x$ | 20 | 3 | Ref. | 2$^+$ | 1$^x$ | 2$^{+++}$ | 1 | 5 |
| Zn$^{2+}$ | 6 | 5 | 20 | 3 | 2 | Ref. | 30 | 5 | 1$^+$ | 5$^x$ | 1$^x$ | 4$^x$ | 2 | 5 |
| Hg$^{2+}$ | 5 | 5 | 20 | 6 | 2 | 1$^+$ | 20 | 4$^x$ | 1$^+$ | 2$^+$ | Ref. | 3$^+$ | 2 | 5 |
| Cd$^{2+}$ | 7 | 10 | 30 | 6 | 5 | 4$^{++}$ | 30 | 5 | 1$^{++}$ | 5 | 2$^{++}$ | Ref. | 1$^{++}$ | 10 |

Ion-sensing system with addition of masking agents of ($^+$) EDTA, ($^{++}$) sodium tartarate, ($^{+++}$) sodium citrate, ($^x$) sodium thiosulfate, (*) potassium cyanide.

Example 11

Stability of UiO-66 Sensor

The actively long-term shelf-time of the MOF sensor efficiency makes the optical strip technologically promising. A long term retention of the MOF sensor was examined under storage for several months [ Balaji T. et al., *Angew. Chem. Int. Ed.* 2006, 45, 7202]. Despite the direct inclusion of the dithizone probe into UiO-66 without the use of the surface modifier, the developed UiO-66 nanomaterials provided control over the potential leaching of the chromophore upon storage. Our results show that little changes in the optically colored density "absorption spectra" of probes From the foregoing description, various modifications and changes in the compositions and methods provided herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A process for detection or recognition of heavy metal ions in an aquatic sample, comprising contacting said sample with a chemosensor and examining said sample for the presence of said heavy metal ions,
   wherein the chemosensor comprises Zr based metal-organic frameworks (Zr-MOF), and
   wherein the presence of said heavy metal ions can be visually detected with the naked eye.

2. The process according to claim 1, wherein the chemosensor comprises Zr-bdc (UiO-66) MOF.

3. The process according to claim 1, wherein the chemosensor comprises Zr-MOF loaded by dithizone (DZ).

4. The process according to claim 1, wherein the chemosensor comprises Zr-bdc (UiO-66) MOF loaded by dithizone (DZ).

5. The process according to claim 1, wherein the chemosensor comprises Zr-bdc (UiO-66)/DZ chromophore.

6. The process according to claim 1, wherein the chemosensor comprises Zr-bdc (UiO-66)/DZ.

7. The process according to claim 1, wherein the chemosensor comprises Zr-bdc (UiO-66)/DZ chromophore prepared by mixing Zr-bdc and DZ.

8. The process according to claim 1, wherein the heavy metal ions are selected from Bi(III), Zn(II), Pb(II), Hg(II), and Cd(II).

9. The process according to claim 1, wherein the heavy metal ions are in dissolved ionic forms.

* * * * *